United States Patent [19]

Boudjouk

[11] 4,447,633
[45] May 8, 1984

[54] ULTRASONICALLY PROMOTED HYDROSILATIONS

[75] Inventor: Philip R. Boudjouk, Fargo, N. Dak.

[73] Assignee: North Dakota State University, Fargo, N. Dak.

[21] Appl. No.: 504,218

[22] Filed: Jun. 14, 1983

[51] Int. Cl.³ .............................. C07F 7/08; C07F 7/18
[52] U.S. Cl. .................................................. 556/479
[58] Field of Search ........................................ 556/479

[56] References Cited

U.S. PATENT DOCUMENTS 2,851,473 9/1958 Wagner et al. ..................... 556/479
3,404,169 10/1968 Gaignon et al. ..................... 556/479
3,624,119 11/1971 Rothe et al. ......................... 556/479

*Primary Examiner*—Paul F. Shaver

[57] ABSTRACT

A method of hydrosilating non-aromatic carbon to carbon pi bonds comprising exposing a mixture of a compound having a said pi bond and a silane having silanic hydrogen to a platinum metal catalyst, and subjecting the mixture to ultrasonic energy while exposed to said catalyst.

9 Claims, No Drawings

ULTRASONICALLY PROMOTED HYDROSILATIONS

FIELD OF THE INVENTION

This invention relates to ultrasonically caused or promoted hydrosilations, and more particularly relates to the ultrasonic acceleration of the hydrosilation of non-aromatic carbon to carbon pi bonds. Illustratively, the invention relates to the ultrasonic acceleration of the reaction between silicon hydrides and compounds containing carbon to carbon pi bonds, whether double or triple, in the presence of a platinum metal catalyst.

The invention is particularly useful in the formation of intermediates or "monomers" (e.g., organosilanes) which may be hydrolized and polymerized to form a variety of silicon-containing products such as silicone resins and elastomers. It also provides a way to make a variety of silicon-containing oils or lubricants in an economical manner. It makes practical several transformations of monomers, or the formation of a variety of monomers having special functional or nonfunctional groups or elements, whether on the silicon atom or on one or more carbon atoms. The principles of the invention may be employed to make new compounds or synthesize known ones in a more economical manner. In essence, the invention provides a way for practical and economical manufacture of organosilanes having varied groups as may be needed or desired for the ultimate manufacture or preparation of a multitude of silicon-containing materials, both organic and inorganic, including silicon carbide.

A great advantage of the invention is that it permits hydrosilation of non-aromatic carbon to carbon pi bonds at relatively low temperatures and under atmospheric pressure.

A great benefit of the invention is that it provides an economical and less time-consuming way to produce comparatively high yields of commercially important organosilanes. Not only are relatively high yields obtained, but isolation of the adduct hydrosilation product in relatively pure form is simple and efficiently accomplished. The conditions employed permit one to avoid the formation of partially polymerized product, as usually is desired. Recoverability of the expensive catalyst is easily accomplished. The catalyst may be reused or recycled many times. Conveniently, the process avoids the need for any solvent or diluent or special medium for the reaction. Normally, only unreacted beginning reagents (including any dispersed catalyst) and the hydrosilation product are present in the mixture after the reaction.

DESCRIPTION OF PRIOR ART

Ultrasonic energy has been employed in a variety of chemical processes other than those involving hydrosilation and has provided varied results; it has accelerated some other types of reactions involving metals.

Hydrosilation reactions have normally required heating to temperatures well above room temperature, generally at least 100° C. and often much higher, in a sealed tube. These addition reactions have also been performed under superatmospheric pressures above about 45 p.s.i. Platinum as a catalyst has been employed and has contributed to an acceleration of known hydrosilations. Nevertheless, the techniques heretofore known either have resulted in comparatively low and variable yields of product, or have required a comparatively long time for reaction, or have required the use of comparatively severe conditions.

SUMMARY OF THE INVENTION

The invention provides a convenient method of hydrosilating non-aromatic carbon to carbon pi bonds. The method involves exposing a mixture of a compound having a non-aromatic carbon to carbon pi bond and a silane having silanic hydrogen to a platinum metal catalyst, and subjecting the mixture to ultrasonic energy while the mixture is exposed to the catalyst.

The use of ultrasonic energy, that is ultrasonic waves, permits the reaction to be carried out under atmospheric pressures and at temperatures generally below about 50° C., usually at or near room temperature.

DESCRIPTION OF PREFERRED EMBODIMENTS

Useful ranges of frequency for ultrasonic energy treatment according to the invention may vary. The most useful frequencies are those at least approaching about 50 KHz, preferably with a concentration or a majority between 40 and 70 KHz. Most experiments were conducted with the major concentration at approximately 55 KHz; but deviation from this range can produce useful results. Extremely simple apparatus may be employed as the generator or source for ultrasonic energy, e.g., a common ultrasonic cleaner for laboratory equipment.

It is to be emphasized that the invention is directed to hydrosilating non-aromatic carbon to carbon pi bonds. As such, one should recognize that the specific compounds or materials containing pi bonds may vary greatly beyond the specific illustrative examples. The principles of the invention may be employed even when the pi bond is not at a terminal location in an alkene or alkyne, although terminal location for the pi bond (that is, a location between carbon atoms at a terminal portion of the compound or material) may frequently be selected as most preferred.

In the following table, eleven specific examples for the practice of the invention are set forth:

TABLE I

| Example | Pi Bond Material | Silane | Time (Hours) | Product | % Yield |
|---|---|---|---|---|---|
| 1 | 1-hexene | $HSiEt_3$ | 2 | $n\text{-}C_6H_{13}SiEt_3$ | 74 |
| 2 | 1-hexene | $HSiCl_3$ | 1 | $n\text{-}C_6H_{13}SiCl_3$ | 90 |
| 3 | 1-hexene | $HSiMeCl_2$ | 1 | $n\text{-}C_6H_{13}SiMeCl_2$ | 95 |
| 4 | 4-methyl-1-pentene | $HSiCl_3$ | 1 | $(CH_3)_2CHCH_2CH_2CH_2SiCl_3$ | 94 |
| 5 | 4-methyl-1-pentene | $HSiMeCl_2$ | 1 | $(CH_3)_2CHCH_2CH_2CH_2SiMeCl_2$ | 96 |
| 6 | 4-methyl-1-pentene | $HSi(OEt)_3$ | 1 | $(CH_3)_2CHCH_2CH_2CH_2Si(OEt)_3$ | 93 |
| 7 | styrene | $HSiCl_3$ | 1.5 | $PhCH_2CH_2SiCl_3$ | 94 |

TABLE I-continued

| Example | Pi Bond Material | Silane | Time (Hours) | Product | % Yield |
|---|---|---|---|---|---|
| 8 | styrene | HSiMeCl$_2$ | 1.5 | PhCH$_2$CH$_2$SiMeCl$_2$ | 94 |
| 9 | 2-methyl-1-pentene | HSiCl$_3$ | 2 | CH$_3$CH$_2$CH$_2$CH(CH$_3$)CH$_2$SiCl$_3$ | 71 |
| 10 | 2-methyl-1-pentene | HSiMECl$_2$ | 2 | CH$_3$CH$_2$CH$_2$CH(CH$_3$)CH$_2$SiMeCl$_2$ | 30 |
| 11 | phenylacetylene | HSiCl$_3$ | 1–2 | PhCH=CHSiCl$_3$ (trans) | 98 |

In the formulas of the table, "Me" refers to methyl, "Et" to ethyl, and "Ph" to phenyl, as done commonly in professional journals.

Each hydrosilation reaction shown in the table, except the reaction for examples 1 and 6, was conducted at approximately 30° C. using a mole ratio of 0.05 for the pi bond material, 0.1 for the silane, and $5 \times 10^{-6}$ for the platinum. The hydrosilations of examples 1 and 6 were conducted at different mole ratios, namely that of 0.1 for the pi bond material, 0.05 for the silane, and $5 \times 10^{-6}$ for the platinum.

All yields of product or monomer are set forth in terms of percent of the theoretically 100% possible yield based on the mole ratios employed. The time for the reaction as set forth in the table is the time that the reaction was allowed to proceed. Optimization of the time may reveal that yields approaching the percentages set forth in the table may be possible within a time less than that listed.

The materials for the reaction were placed in a 100 milliliter single neck flask fitted with a condenser and nitrogen inlet and partly submerged in the bath of a common ultrasonic laboratory cleaner (e.g., a Bransonic Model 220) which provided a concentration of frequencies between about 40 and 70 KHz with the major concentration at approximately 55 KHz. The ultrasonic bath temperature was maintained at about 30° C. by employing a fan to blow room temperature air against the side of the vessel holding the bath. Had this not been done, the temperature of the bath would have gradually risen above about 30° C. as a result of the ultrasonic energy or the exotherm of reaction; however, it was noted that the reactions proceed smoothly without vigorous exotherm. The flask was positioned or adjusted in location in the bath to produce the greatest agitation of the reaction mixture. The greatest agitation was noted to cause a vigorous bubbling action in the flask and the generation of a misty cloud above the liquid. All reactions were conducted under atmospheric pressure.

After removal of the vessel from the bath at the end of the time period noted in the table, the contents of the vessel were filtered to remove the platinum catalyst. The filtrate then was distilled; and the unreacted pi bond material and silane were each collected, followed by collection of the resulting product as set forth in the table. Product identification was made according to known standards, e.g., infrared spectroscopy, nuclear magnetic resonance spectroscopy, and mass spectroscopy.

While platinum on carbon was employed as the form for the platinum metal catalyst, other forms of platinum or an equivalent platinum metal catalyst such as rhodium or ruthenium or iridium may be employed with satisfactory results. Preferably the platinum metal catalyst should be in a form providing a high surface area for its mass; and this is easily accomplished by employing a carrier for it such as carbon particles or by employing it in finely divided form or even in strip form. Intimate exposure of the reactants to the catalyst is necessary for the most efficient hydrosilations.

Note should particularly be made of Example 1 set forth in the table. Triethylsilane is known to be a silane which adds to olefins only with great reluctance even in the presence of platinum and even when employing high temperatures and pressures (that is, even when employing "forcing" conditions). Nevertheless, as illustrated in Example 1, and with the reaction conducted at relatively low temperatures and under atmospheric pressure, a high yield of the hydrosilation product was obtained. Typically, referring to Example 1, 5.8 grams (0.05 mole) of triethylsilane, 8.4 grams (0.1 mole) of 1-hexene, and 0.1 gram of 1% platinum on carbon ($5.1 \times 10^{-6}$ mole of platinum) were mixed in a flask and subjected to the ultrasonic conditions aforedescribed. The yield of hydrosilation product was 7.4 grams or 74%; it had a boiling point of about 50° C./0.02 torr. The significance of Example 1, apart from demonstrating the unusual effectiveness of the process described herein, is that it illustrates an approach useful for the preparation of a variety of silicon-containing lubricants (e.g., peralkylated silanes).

Example 6 of the table should also be particularly noted. Triethoxysilane adds very efficiently and quickly to the pi bond when practicing the invention but relatively poorly and slowly at room temperature without ultrasonic treatment.

With respect to Examples 9 and 10, the more sterically hindered olefin, 2-methyl-1-pentene, should be noted as one relatively difficult to hydrosilate. Even so, relatively substantial yields of this adduct product were obtained, and within a relatively short time.

Likewise of importance is the illustration set forth at Example 11, where phenylacetylene proved to be a very easy substrate for hydrosilation (and produced trans-trichlorosilylstyrene) under the ultrasonic conditions illustrated even though it is difficult to hydrosilate and gives poor yields without ultrasonic treatment.

Worth emphasis, particularly with respect to Examples 1, 6, 9, 10 and 11 (but also significant as regards the other Examples), is that in the absence of ultrasonic waves or energy as illustrated, no significant reaction at temperatures below 50° C. was observed for any of these examples unless the reagents were vigorously agitated for at least 10 hours. Even then the yields of the adduct hydrosilation product were usually below about 5%.

Useful silanes for practice of the invention must have silanic hydrogen, that is a hydrogen bonded to the silicon atom. Generally, the silanes will be of the formula $$R_{3-n}SiH_{1+n}$$

wherein R is a halogen (preferably chlorine), a lower alkoxy (preferably having no more than 4 carbon atoms), a lower alkyl (preferably no more than 4 carbon atoms), a substituted alkyl or alkoxy (that is, one containing a functional group such as amino, halo, carboalkoxy, alkene, alkyne, cyano, carboxylic acid, alkoxy, carbonyl group, or a substituted silane), a phenyl, or mixtures thereof; and n is 0, 1, or 2. Thus, up to three silanic hydrogens may be on a silicon, although only one is necessary. Polymerizable hydrosilation products, especially those polymerizable to polysiloxanes, should be formed using a silane wherein at least two R groups on the silicon are a halogen or alkoxy or both (that is, where functional groups for further reaction are on the silicon); but some R groups of the silane employed to make polymerizable products may be alkyl or phenyl. If only one functional group such as a halogen or alkoxy is employed on the silicon, the resulting product is capable of being dimerized, but may be polymerized if other functional groups for polymerization are included on the radical added through the pi bond.

The reagent providing the non-aromatic carbon to carbon pi bond to be hydrosilated preferably contains more than just the two carbon atoms of a pi bond. While the pi bond must be non-aromatic, reagents which include an aromatic nucleus (e.g., Examples 7, 8, and 11) are useful. Steric hindrance is a factor to consider where a bulky group is close to or on a carbon of a pi bond; but from a comparative standpoint, even though yields may be relatively reduced under such circumstances, the method of the invention nevertheless affords a route for relatively improved and significant hydrosilation of such compounds. The pi bond may be a double bond (e.g., olefinic or an alkane type) or a triple bond (an alkyne type); and in a generic sense aliphatic pi bond compounds having more than 4 carbon atoms are most preferred since one of the purposes of the process is to create new and larger or substituted silane type products as a result of the hydrosilation. To be emphasized is that the pi bond compounds may include a variety of functional elements or groups providing sites for further reaction or removable in subsequent processing to provide a remaining site for further reaction; and in this sense, the pi bond compounds are not limited to pure hydrocarbons.

Substituents or groups in either or both the silanic hydrogen silane reagent or the pi bond compound may vary from those illustrated. Thus, the specific examples are intended to be illustrative but not limitative; and in this respect, the claims appended hereto and made a part of this disclosure should be construed as broadly, including equivalents known or hereafter developed, as consistent with their validity.

That which is claimed is:

1. A method of hydrosilating non-aromatic carbon to carbon pi bonds comprising exposing a mixture of a compound having a said pi bond and a silane having silanic hydrogen to a platinum metal catalyst, and subjecting the mixture to ultrasonic energy while exposed to said catalyst.

2. The method of claim 1 wherein said silane has the formula $$R_{3-n}SiH_{1+n}$$

wherein R is selected from the group consisting of a halogen, a lower alkoxy, a substituted alkoxy, a lower alkyl, a substituted alkyl, a phenyl, or mixtures thereof, and n is 0, 1, or 2.

3. The method of claim 2 wherein the selection for R of said silane includes a halogen or a lower alkoxy or both.

4. The method of claim 1 wherein said compound having a said pi bond contains more than two carbon atoms.

5. The method of claim 1 wherein said compound having a said pi bond is selected from the group consisting of alkenes and alkynes.

6. The method of claim 1 wherein said compound having a said pi bond is aliphatic and contains more than four carbon atoms.

7. The method of claim 1 wherein said compound having a said pi bond comprises an olefinic compound.

8. The method of claim 1 wherein said compound having a said pi bond includes an aromatic nucleus.

9. The method of claim 1 wherein said compound having a said pi bond comprises phenylacetylene.

* * * * *